US00PP08577P

United States Patent [19]

De Meyer

[11] Patent Number: Plant 8,577

[45] Date of Patent: Feb. 1, 1994

[54] GUZMANIA PLANT NAMED MANDARINE

[75] Inventor: Henri De Meyer, Destelbergen, Belgium

[73] Assignee: H. De Meyer, Laarne, Belgium

[21] Appl. No.: 893,817

[22] Filed: Jun. 4, 1992

[51] Int. Cl.[5] ..... A01H 5/00

[52] U.S. Cl. ..... Plt./88/6

[58] Field of Search ..... Plt. 88.6

*Primary Examiner*—James R. Feyrer

*Assistant Examiner*—Elizabeth C. Kemmerer

*Attorney, Agent, or Firm*—Foley & Lardner

[57] ABSTRACT

A new and distinct cultivar of Guzmania plant named Mandarine, characterized by its bright orange red bracts in the center of the plant which extend generally horizontal in the upper ends thereof to form a more open show of color; lower green leaves which provide a striking contrast with the orange red bracts; purplish striping on the top surface of leaf sheaths of new leaves, and its long lasting flowers.

2 Drawing Sheets

SUMMARY OF THE INVENTION

The present invention comprises a new and distinct cultivar of *Guzmania minor* x *sanguinea*, referred to by the cultivar name Mandarine. The genus Guzmania is within the family Bromeliaceae.

Mandarine is a product of a planned breeding program conducted in Laarne, Belgium. The program evolved from the importation by the inventor of seeds of several different cultivars of *Guzmania sanguinea* from Colombia. When grown out to flower, several plants were selected for their beautiful flowers, and were subsequently crossed with cultivars of the species *Guzmania minor*.

Mandarine was originated by the inventor Henry De Meyer from a hybridization made in the program in Laarne, Belgium. The female parent was an unnamed proprietary *Guzmania minor* cultivar identified as "red". The male parent of Mandarine was an unnamed *Guzmania sanguinea* cultivar.

Mandarine was discovered and selected by the inventor after flowering in early 1990. The new cultivar was thereafter asexually reproduced from offshoots under the supervision of the inventor in a controlled environment in Laarne, Belgium. The offshoots can be rooted with the resulting plantlets being detached from the mother plant and potted up in an appropriate growing mixture.

Horticultural examination of plants so propagated has demonstrated that the combination of characteristics as herein disclosed for Mandarine are firmly fixed and retained through successive generations of asexual reproduction, which can be effected by offshoots as described, or by known tissue culture techniques.

Although asexual or vegetative propagation is an effective replication technique, it has been discovered that both parents have a high degree of homozygosity so that the progeny of the cross were and continue to be surprisingly uniform.

Mandarine has not been observed under all possible environmental conditions. The phenotype may vary significantly when grown under different conditions of temperature, light, and other determining factors, without, however, any variation in genotype. The following observations, measurements and comparisons describe plants grown in Laarne, Belgium under greenhouse conditions which approximate those generally used in commercial practice.

The following traits have been repeatedly observed and are determined to be basic characteristics of Mandarine which in combination distinguish this Guzmania as a new and distinct cultivar:

1. Mandarine has bright orange red bracts in the center of the plant, which, together with the lighter orange flowers, give a very unique and striking effect. The lowermost bracts have a green tip and a grey-green zone which merges the green tip and the orange inner colors.
2. The lower leaves are primarily green in color and provide a remarkable contrast with the orange center and top of the plant.
3. The inflorescence is long lasting.
4. The leaf sheaths are well formed and closely linked at the base, and are generally the same green color as the leaves. However, the sheaths of the new leaves has a distinctive fine purplish violet stripe pattern on its top surface.
5. Intermediate their length but somewhat closer to their base, the bracts curl outwards to from a generally horizontal plane, with the plane of the newest bracts being lower than the somewhat older bracts.

BRIEF DESCRIPTION OF THE APPLICATION DRAWINGS

The accompanying photographic drawings show the inflorescence and foliage characteristics of Mandarine as clearly as possible. The photo on the first sheet comprises a top perspective view of a substantial part of a plant of Mandarine in bloom. The photo on the second sheet comprises a top view showing the inflorescence in more detail. The colors are as nearly true as possible with illustrations of this type.

DETAILED DESCRIPTION

Mandarine can be compared in certain respects to the commercially available *Guzmania minor* 'Empire.' Mandarin is similar to Empire with respect to size and color of green foliage. Mandarine is distinguished from Empire by Mandarine's orange red bracts that extend to the heart of the plant, thicker flower stems, larger flowers, faster growth, and longer lasting habit. Because of the overall uniqueness of Mandarine, a meaningful comparison with other cultivars of the same type is difficult.

In the following description, color references are made to The Royal Horticultural Society Color Chart. The color values were determined at Laarne, Belgium.

Classification:

*Botanical.—Guzmania minor* x *sanguinea cv. Mandarine.*

PLANT

Form: Rosette.

Height: Approximately 15 cm when plant is in bloom. The leaf rosette has a height of approximately 11 cm.

Diameter: Approximately 45 cm when plant is in bloom.

Growth habit: Stemless.

Method of propagation: By offshoots or tissue culture.

Foliage:

*Quantity.*—Rosette is comprised of approximately 20 leaves having a length from 5 to 30 cm. The oldest leaves are much shorter (8 cm) than the new ones formed.

*Size.*—Bottom leaves have a width of 2.1 cm and top leaves have a width of about 2.8 cm. Length varies as noted above.

*Shape.*—Linear with a pointed tip; leaf edge is entire and upright.

*Surface texture.*—Smooth, both top and bottom surfaces.

*Color.*—Both top and bottom sides are approximately 137B.

*Leaf sheaths.*—Well formed and closely linked at the base; they are oval and approximately 6×6 cm in size. Color similar to leaf color. A distinctive feature of the leaf sheaths of the newer leaves is a narrow purple violet stripy pattern (RHS 185A) on the top side of the sheath.

BRACTS

Quantity: Approximately 20 in number, with the base of the bracts completely surrounding the flower shaft. The top bracts rise above and surround the flower.

Size: Bracts at bottom of the flower shaft are approximately 16 to 20 cm in length and 2 to 3 cm in width; bracts near top of flower shaft have a length of 10 to 15 cm and a width of 1.5. to 2 cm.

Shape: At approximately one-third of the length of the bracts, the leaf curls outward so that the bracts of one and the same verticil form a generally horizontal plane, with the plane of the newest bracts being below the plane of the somewhat older bracts. This provides a substantially more expanded or open appearance.

Color: The lowermost verticil of bracts have a green tip and a grey-green merge zone (closest to RHS 197A) between the tip and the orange inner portion of the leaf. The upper bracts are solid orange red closest to 32A-33B, both top and bottom sides.

FLOWERS

Borne: On short and sturdy shafts which stand erect and which have a diameter of approximately 2 cm and a length of about 7 cm.

Blooming habit: Flowers bloom approximately 13 weeks after induction. Single flowers bloom only one day, and total inflorescence lasts approximately eight (8) weeks.

Quantity: 10 to 30.

*Size.*—The entire flower system has a length of approximately 6 cm and a diameter of 3 to 4 cm. Each individual flower is about 4–5 cm in length and 5–6 mm in diameter.

*Shape.*—Straight.

*Color.*—Yellow-orange approximately 17B-C with white top.

*Petals.*—White in color and visible when the plants are in bloom petals are fused.

*Seed capsule.*—A reddish brown pyxidium of about 3 cm is formed.

*Reproductive organs.*—Pistil: 1, white. Stamens: 6, white.

I claim:

1. A new and distinct cultivar of Guzmania plant named Mandarine, as illustrated and described.

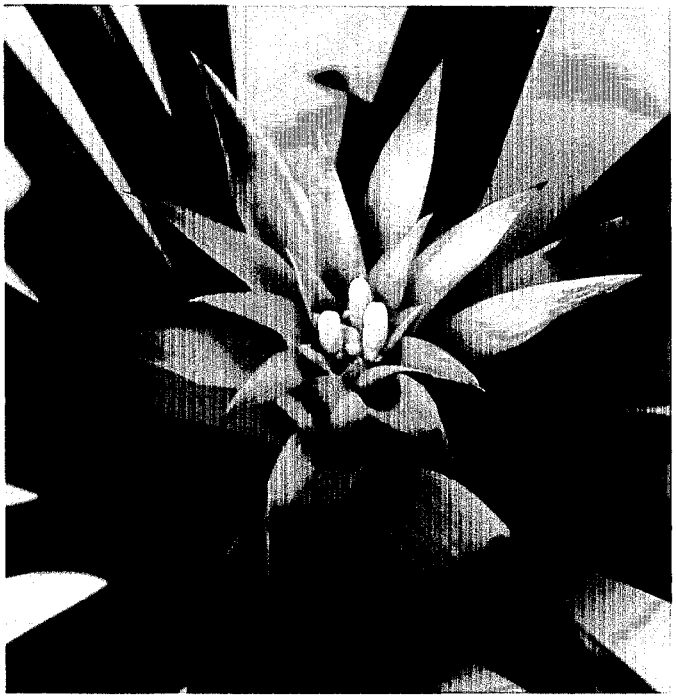

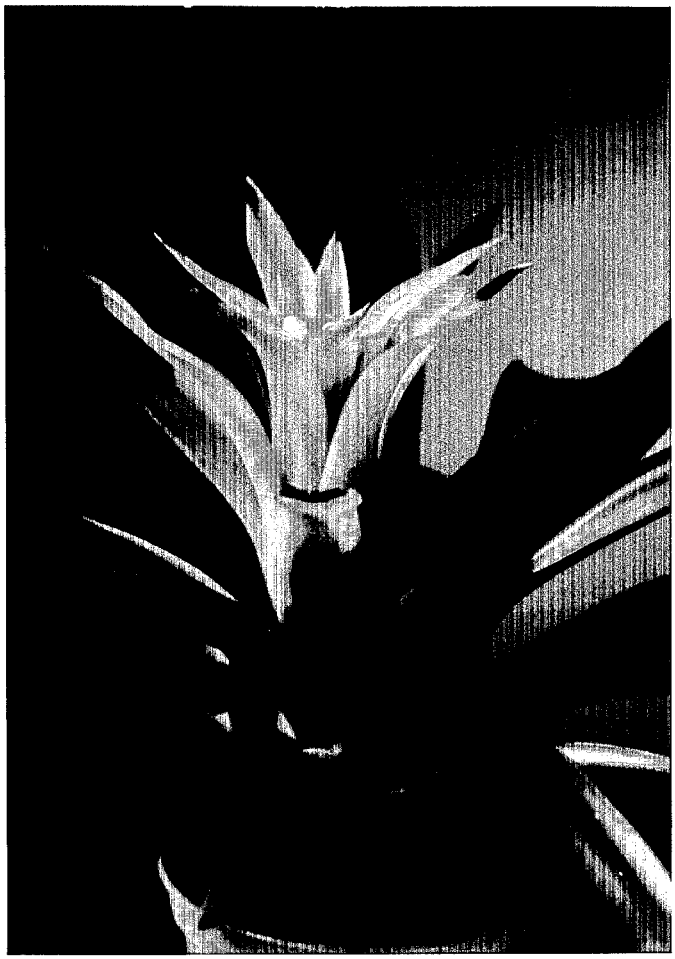

* * * * *